United States Patent [19]

Lardinois et al.

[11] Patent Number: 4,983,510
[45] Date of Patent: Jan. 8, 1991

[54] ENZYMES IMMOBILIZED ON LATEX POLYMER PARTICLES FOR USE WITH AN AMINO ACID ELECTROSENSOR

[75] Inventors: Pierre F. Lardinois; Paul G. Rouxhet; William E. E. Stone, all of Louvain-la-Neuve; Kenneth M. Baker, Brussels; Alain E. Baudichau, Tourinnes-la-Grosse, all of Belgium

[73] Assignee: Monsanto Company, St. Louis, Mo.

[21] Appl. No.: 262,862

[22] Filed: Oct. 26, 1988

[30] Foreign Application Priority Data

Oct. 29, 1987 [GB] United Kingdom ............... 8725333

[51] Int. Cl.$^5$ .................. C12Q 1/00; C12Q 1/26; C12N 11/08; C12M 1/40
[52] U.S. Cl. ...................................... 435/4; 204/403; 435/18; 435/25; 435/180; 435/288; 435/817
[58] Field of Search ................. 435/4, 18, 25, 180, 435/181, 817, 288; 204/403

[56] References Cited

U.S. PATENT DOCUMENTS 4,064,080 12/1977 Daniel ........................................ 260/8
4,195,129 3/1980 Fukui et al. ............................ 435/182
4,415,700 11/1983 Batz et al. ........................... 436/533 X

FOREIGN PATENT DOCUMENTS 0075815 4/1983 European Pat. Off. .

OTHER PUBLICATIONS

Chemical Abstracts, vol. 86, No. 17, 4/25/77, p. 190, 86:116829g.
Chemical Abstracts, vol. 98, No 17, 10/27/80, p. 495, 93:166016e.
Bahadur et al., Makromol. Chem. (1985) 186, 1387.
Hoshino et al., Kobunshi Ronbunshu, (1985), 42 (5) 305.
Ianniello and Yacynych, Anal. Chim. Acta (1983), 146, 249.
Fung et al., Analytical Chemistry, (1979) 51, 2319.

Primary Examiner—David M. Naff
Attorney, Agent, or Firm—James W. Williams, Jr.; Stanley M. Tarter; Charles E. Smith

[57] ABSTRACT

Enzymes such as L-methionine gamma lyase, L-lysine decarboxylase, L-aspartase and L-tryptophanase are immobilized by contacting with a latex of polymer particles having a negative surface charge such that the electrophoretic mobility of the latex has a negative value of $-2.0\ 10^{-8} m^2 V^{-1} sec^{-1}$ or below when measured at pH 7 in 0.01M $KNO_3$ and a polymer solids concentration of 30 mg/l. The polymer particles also have a hydrophobic surface such that the contact angle of a 1 microliter droplet of distilled water with a plane horizontal surface formed by drying and compacting the latex particles is 70° or more. The resultant-enzyme/polymer particles can be used for assaying amino acids corresponding to the specific enzyme immobilized in aqueous solutions using an electrosensor comprising a pH-sensitive electrode located in a sensing zone or chamber containing the enzyme/polymer particles as an aqueous dispersion or in water-dispersible form.

5 Claims, 6 Drawing Sheets

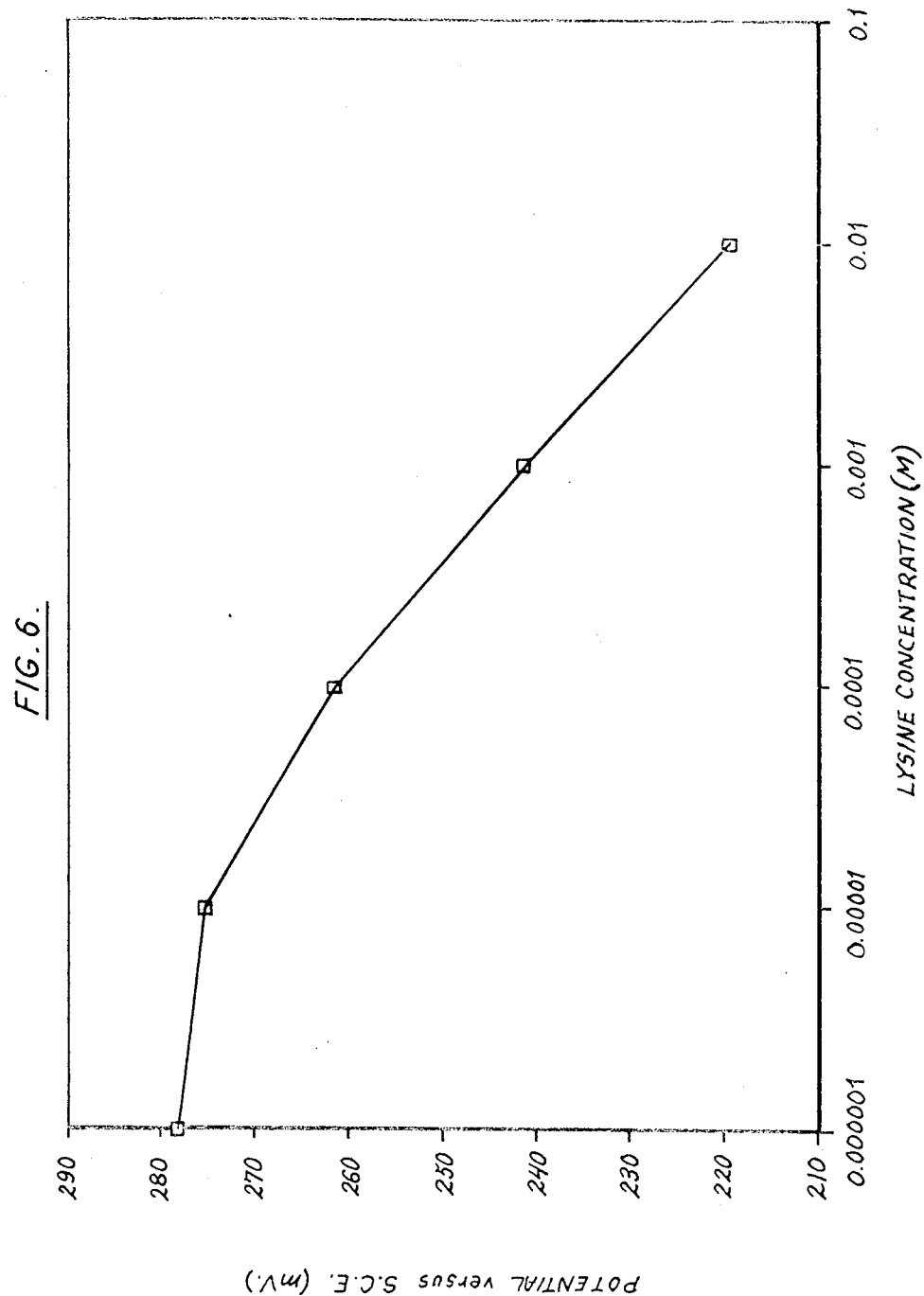

ENZYMES IMMOBILIZED ON LATEX POLYMER PARTICLES FOR USE WITH AN AMINO ACID ELECTROSENSOR

BACKGROUND OF THE INVENTION

1. Field of the Invention

This invention relates to the immobilisation of enzymes, more particularly to the immobilisation of enzymes suCh as L-methionine gamma-lyase and L-lysine decarboxylase. The invention also relates to an electrosensor for assaying amino acids in solution, comprising a pH-responsive electrode in combination with an immobilised enzyme which degrades the aminoacid with an acCompanying change in the pH of the solution.

2. Prior Art

Immobilised enzymes and their role in biocatalytic reactions are of considerable technological importance. Carriers which have been used to immobilise enzymes include polymer latices. In most instanCes, the polymers concerned have been derived from monomers or comonomers containing, functional groups. For instance U.S. Pat No. 4,064,080 discloses latices of styrene polymers having terminal aminophenylthio groups for immobilising proteins; Bahadur et al, Makromol. Chem. (1985), 186, 1387 describe core-shell latices of poly(-methyl methacrylate-co-acrylic acid) having carboxyl groups on the surface of the polymer particles, and the immobilisation of alpha-chymotrypsin on the surface of the latex particles by chemical bonding using a carbodiimide coupling agent; and Hoshino et al, Kobunshi Ronbunshu, (1985), 42 (5), 305 describe the use of hydrolysed styrene-N-hydroxymethyl acrylamide copolymer latices to immobilise alpha-amylase.

The use of pH sensors to monitor enzyme-catalysed decompositions has also been described in the literature. For example Ianniello and Yacynych, *Anal. Chim. Acta* (1983), 146, 249 report the use of an iridium dioxide-coated metal, for example titanium, as a pH responsive electrode for monitoring the decomposition of urea by urease. The urease was immobilised on to the iridium oxide by physical entrapment in a poly(vinyl chloride) film or by a covalent attachment via a cyanuric chloride linkage.

Fung et al, Analytical Chemistry, (1979) 51, 2319 describe a potentiometric enzyme electrode for the assay of methionine in solution. It was prepared by coating a layer of methionine lyase immobilised in bovine serum albumin cross-linked with glutaraldehyde on to an ammonia gas sensing electrode.

The non-covalent bonding of enzymes to a support surface is often a reversible process, and the equilibrium concentration of adsorbed enzyme may not be a useful amount. Moreover, enzyme which is adsorbed is frequently at least partially deaCtivated by distortion of its structure by bonding forces. The problem of deactivation by distortion can be particularly acute where regions of the enzyme are covalently bonded directly or through a bonding agent to functional groups on the surface of the support. This means that the desirable objective of immobilising an enzyme on a support without substantial loss of activity can only be met where there is a high degree of specificity between the enzyme, the support and the way in which they are linked.

In previously described biosensor devices comprising a sensor electrode in combination with an immobilised enzyme, the enzyme has been present as a dispersion in a relatively rigid film of polymeric material on the surface of the electrode or as a covalently-bonded coating on the surface of the electrode. Immobilisation in a rigid film imposes limitations on the accessibility of the substrate to the enzyme and on the reproducibility of such devices. The use of covalent bonding to immobilise the enzymes on the electrode surface restricts the amount of enzyme available in the system, while both methods of immobilisation limit the speed of response of the device.

BRIEF SUMMARY OF THE INVENTION

We have found that the enzymes L-methionine gammalyase and L-lysine decarboxylase can be immobilised, with high enzyme activity retention, on polymer particles having defined characteristics. The same polymer particles can be used, somewhat less effectively, for the immobilisation of aspartase and of tryptophanase. Such particles carrying the immobilised enzyme can be used in conjunction with a pH-responsive electrode for the assay of the corresponding aminoacids in solution.

BRIEF DESCRIPTION OF THE DRAWINGS

FIG. 6 is a graphic illustration of the potential difference, after addition of enzyme, against concentration of L-lysine.

DETAILED DESCRIPTION OF THE INVENTION

Figure 1A:
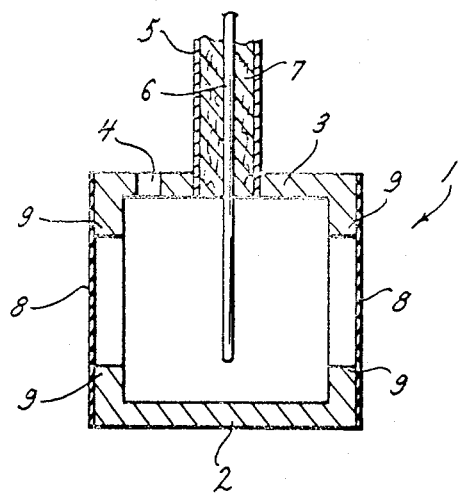
FIG. 1(a) is a cross-section view of an electrolytic half-cell which may be utilized to determine an aminoacid in accordance with the present invention.

Accordingly, the invention provides a method for the immobilisation of an enzyme selected from L-methionine gamma-lyase, L-lysine decarboxylase, aspartase and tryptophanase, which comprises contacting the enzyme with a latex of polymer particles having a negative surface charge such that the electrophoretic mobility of the latex has a negative value of $-2.0 \cdot 10^{-8} m^2 V^{-1} sec^{-1}$ or below (i.e. more negative) when measured at pH 7 in 0.01 M $KNO_3$ and a polymer solids concentration of 30 mg/l, the polymer particles also having a hydrophobic surface such that the contact angle of a 1 microliter droplet of distilled water with a plane horizontal surface formed by drying and compacting the latex partiCles is 70° or more.

The invention further includes an electrosensor for use in assaying an aminoacid seleCted from L-methionine, L-lysine, L-aspartic acid and tryptophan, said electrosensor comprising a pH-responsive electrode located in a sensing zone containing polymer particles which have had an enzyme immobilised thereon by the method of the invention, the said particles being present as an aqueous dispersion or in water-dispersible form.

The electrosensor of the invention has the advantage over previously described biosensors for enzymes that although the enzyme is immobilised on the surface of the polymer particles, the particles themselves are mobile or potentially mobile within the sensing zone. Access of the substrate to the enzyme is thereby vastly improved in comparison with previous systems in which the enzyme carrier is itself immobile.

Latices which can be used in the method of the invention can, for example, have an average particle size in the range 0.1 to 5 micrometers. Preferred latices have particles with an average size in the range 0.3 to 3 micrometers, more especially 0.6 to 1 micrometer.

For certain applications, including use in the electrosensor of the invention, particles having a relatively narrow size distribution are preferred. Particles in latices produced by the emulsion polymerisation of monomers typically meet this last requirement.

Many polymers are produced by emulsion or suspension polymerisation of a monomer or monomers using persulphate as a component of the polymerisation catalyst. This results in the presence of a small number of residual ionic groups derived from the persulphate catalyst, for example $-O-SO_3^-$, on the latex particles. In the absence of cationic surface groups, such groups confer a negative surface charge on the particles. Where the monomer or monomers from which the polymer is derived is non-polar, or substantially so, the residual anionic groups following a persulphate-catalysed polymerisation are normally sufficient to provide a latex having an electrophoretic mobility within the range required in the method of the invention. Good results have been obtained using latices of polystyrene and of a copolymer of styrene with a small amount of carboxylic monomer, for instance acrylic or methacrylic acid. As is well known, however, styrene will copolymerise in various proportions with a wide range of comonomers. It is believed that any of the considerable number of such copolymer latices could be used to immobilise enzymes in accordance with the method of the invention provided that the copolymer particles have a negative surface charge and a hydrophobicity as defined above.

It is also possible to modify the surface of the latex particles by mixing the latex with solutions of ionic or polar substances and then recovering and redispersing the modified latex particles. For example solutions of metallic salts, especially salts of multivalent metals such as aluminium, iron, titanium or zinc, or polar and ionic polymers such as chitosan, can be used for this purpose. The amounts of such modifiers used and the conditions of modification should be such that the electrophoretic mobility and hydrophobicity of the modified latex are within the limits specified above.

Preferably, latices for use in the invention have electrophoretic mobilities of from about $-3.5$ to about $-6.5$, for example from about $-4.5$ to about $-5.5$, $10^{-8} m^2 V^{-1} sec^{-1}$ when measured at pH 7 in 0.01 M $KNO_3$ and a polymer solids concentration of 30 mg/l, and hydrophobic surfaces such that the aforesaid contact angle is from 70° to 150°, for example from 100° to 130°.

In the electrosensor of the invention, unlike the prior art electrosensors, the immobilised enzyme is not present in a rigid film coated on to the surface of the electrode. It is however confined to a sensing zone in which the pH-responsive electrode is located. In one embodiment, the electrosensor comprises a half cell adapted for use in conjunction with an exterior reference electrode. The sensing zone is within a container constructed of materials such that when the container contains and is surrounded by a solution containing the aminoacid to be assayed, latex particles with adsorbed enzyme are retained within the container, but the aminoacid can diffuse into and out of the container.

In another embodiment, the electrosensor comprises a container containing latex particles with adsorbed enzyme, and is adapted to accommodate both a pH-sensitive electrode and a reference electrode.

The invention further includes a method of assaying an aminoacid, which comprises introducing a solution containing the aminoacid into the sensing zone of an electrosensor of the invention, said solution being in contact with a reference electrode, and said sensing zone also containing pyridoxal-5-phosphate as a coenzyme, measuring the change in the potential difference between the pH- responsive electrode and the reference electrode over a fixed time interval and correlating the said change with the amount of aminoacid in the solution.

In the drawings, FIG. (1) a shows a cross-section through an electrolytic half-cell which can be used to determine an aminoacid in accordance with the invention. FIGS. 1(b) and 1(c) show cross-sections of electrolytic cells useful for the same purpose. FIGS. 2–6 illustrate graphically various results obtained in the Examples set out below.

Figure 1B:
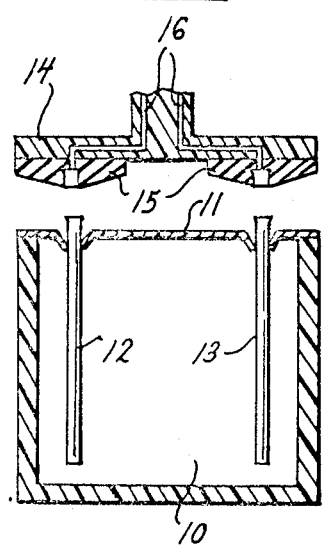
FIG. 1(b) is a cross-section view of an electrolytic cell which may also be utilized to determine an aminoacid in accordance with the present invention.
Figure 1C:
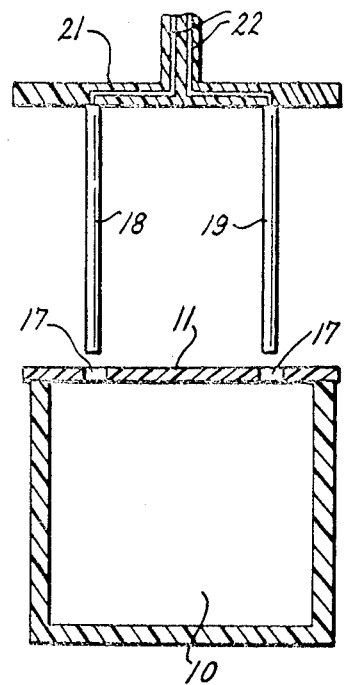
FIG. 1(c) is a cross-section of an alternate electrolytic cell which may be utilized.

The half-cell of FIG. 1(a) comprises a generally cubic chamber (1), of which the lower horizontal face (2) is continuous. Size is not critical, but the half-cell used in the experiments described in the Examples below had an external dimension of approximately 2.5 cm. The upper horizontal face (3) has an opening (4) to provide access to the interior of the chamber, and is attached centrally to a cylindrical sleeve (5) within which a pH-sensitive wire electrode (6) is held coaxially by means of packing (7). The vertical faces of the cube have square cut-out areas which are covered with semi-permeable membranes (8) attached to the edges (9) of the vertical faces of the cube. The dimensions of the cubic chamber are not critical; that used in the Examples described below had an outside dimension of approximately 27 mm and a wall thickness of approximately 2 mm. All materials of construction except the wire electrode are electrically non-conductive. Various polymeric materials, e.g. polypropylene, poly(tetra-fluoroethylene), polycarbonates, acrylonitrile-styrene-butadiene polymer blends or polyamides can be used. Rislanμ, which is a blend of nylon 11 and nylon 12, has been found to be particularly suitable. pH-sensitive wire electrodes comprise a metal oxide coating on a metal wire, and various combinations have been described in the literature. In the half-cell used in the Examples below, the pH-sensitive wire electrode consisted of a titanium wire coated with iridium oxide with a further external coating of a fluoro-sulphonyl copolymer (see U.S. Pat. No. 4,536,274). The semi-permeable membranes are required to retain latex particles but to be permeable to aminoacids. Membranes of cellulose acetate and of a polycarbonate film having a pore size of 0.45 micrometers, each having a thickness of about 10 micrometers, have been found to be suitable. In FIGS. 1(b) and 1(c), each cell comprises a container (10) with a lid (11), both made from a plastics material such as polypropylene or polystyrene. The container is conveniently cylindrical in shape, with a typical external diameter of approximately 10 mm and a typical height of 7 mm. In the cell of FIG. (b), a pH-sensitive wire electrode (12) and a reference electrode (13), typically a silver chloride-coated silver wire, are fixed as inserts through the lid (11). A connector (14) has terminals (15) which are adapted to make a push fit over the upper ends of the electrodes (12) and (13) exterior to the lid of the container, and has conductive means (16) to connect the terminals (15) with a pH meter. The lid can be made to be removable, or alternatively, it can be of a thickness which can be penetrated by a hollow needle so that liquids can be injected into the container from a syringe.

In the cell of FIG. 1(c), the lid (11) has two openings (17) which permit the insertion of a pH-sensitive wire electrode (18) and a reference electrode (19), the electrodes being inset at their upper ends into a disc or bar (20) of electrically insulating material which forms part of a connector (21). When the cell is in use, the disc or bar is adapted to rest on the lid of the container. The connector (21) is also provided with conductive means (22) to connect the electrodes with a pH meter.

In the Examples described below, two latices, Estapor$\mu$ latex K109 (A) and Estapor$\mu$ latex PSI 480 (B), both manufactured by Rhône-Poulenc, were used. Each is described by the manufacturers as a polystyrene latex containing 10% by weight of solids in suspension and a particle diameter of approximately 0.80 micrometers, with latex B additionally having carboxyl surface functional groups.

Various characteristics of the latices were investigated using X-ray photoelectron spectroscopy (XPS), infra-red spectroscopy (IRS), microelectrophoresis, and contact angle measurements. To obtain samples for XPS, IRS and contact angle measurements, the original latices were washed by centrifugation and resuspension twice in distilled water. The final sediment was freeze dried.

For XPS, the powder was pressed with a spatula in stainless steel troughs (B mm in diameter), the surface being smoothed with the spatula. For contact angle measurements, ten wells (4 mm in diameter, 0.3 mm deep) hollowed in a polyacetal plate were filled in the same way. For recording IR spectra, thick paper with a hole of 5 mm diameter was used as the sample holder; the latex powder was placed in the hole and pressed under a pressure of about 30 MPa.

XPS spectra were recorded with a Vacuum Generator ESCA 3 spectro-meter interfaced with a Tracor Northern Signal accumulator using a non-monochromatized Mg K source (14 kV, 20 mA). The analysis energy was 50 eV and the electron take-off angle 45°.

All functional groups were assumed to be localised at the surface of the latex particles, and quantitative surface analysis was carried out using the integrated surface of the peaks and the empirical sensitivity factors of Wagner et al. (Surf. Interface Anal., (1981), 3(5), 211-225) and Wagner, (J. Electron Spectrosc. Relat. Phenom., (1983), 32, 99-102).

The XPS spectra of all latices were dominated by the peak of $C_{1s}$ electrons, the binding energy (BE) of which was set at 285.0 eV and served as reference for the energy scale. The spectra showed an $S_{2p}$ peak, with a BE between 168.7 eV and 169.7 eV, which is typical of groups ($-OSO_3^-$) The presence of such groups on the surface of all latices was attributed to the initiation of polymerization by $S_2O_8^{31}$ which produces $SO_4^{31}$ radicals; a $-O-SO_3^-$ group remains attached at each end of the polymer chain. An $O_{1s}$ peak, between 532.5 eV and 533.5 eV, contained a contribution of oxygen from $-O-SO_3^{31}$ groups and from carboxyl groups.

The mean values of atomic concentration ratios ($C_x/C_c$) (x=oxygen or sulphur) in latex samples and calculated values for the superficial concentrations of oxygen and sulphur atoms, (O) and (S) are given in Table 1 below.

TABLE 1

| Latex | $C_s/C_c$ | $C_o/C_c$ | $(S) nm^{-2}$ | $(O) nm^{-2}$ |
|---|---|---|---|---|
| A-sample 1 | 0.0013 | 0.011 | 0.10 | 0.46 |
| A-sample 2 | 0.0011 | 0.015 | 0.09 | 0.62 |
| B-sample 1 | 0.0020 | 0.018 | 0.16 | 0.75 |
| B-sample 2 | 0.0015 | 0.019 | 0.12 | 0.79 |

Infrared absorption spectra (2000 to 1500 cm$^{-1}$) were recorded on a Perkin Elmer 580 B spectrophotometer equiped with a Data Station microprocessor. The intensity of the whole spectrum was normalised by setting the absorbance at 1945 cm$^{-1}$ at a given value, thus eliminating the effect of variations in pellet thickness. The contribution of the carboxyl groups at 1750-1700 cm$^{-1}$ was determined by subtracting the spectrum of a polystyrene latex containing no carboxyl. Calculated surface concentrations of carboxyl groups (groups nm$^{-2}$) were: Latex A, sample 1, 0.17; Latex B, sample 1, 0.33; Latex B, sample 2, 0.4.

The microelectrophoretic mobilities of the latices were measured with a Lazer Zee-Meter 500 (Pen-Kem) in a rectangular polymethyl-methacrylate cell. The total volume of suspension introduced was about 25 ml. The applied voltage was 30 to 50 V.

Electrophoretic mobilities were determined at various pH values in both 0.01 M and 0.001 M KNO$_3$. They were also determined in the L-methionine gamma lyase medium diluted 10 times (0.01 M in phosphate) (MGL) and in the lysine decarboxylase medium diluted twice (0.01M in phosphate) (LD). Both latices were negatively charged from pH 3 to pH 10.

Values for electrophoretic mobility (with an uncertainty factor of ±0.5 unit of mobility*) at pH 7.0 ±0.2 are given in Table 2 below.

TABLE 2

| Medium<br>Latex | KNO$_3$ 0.001 M<br>pH 7 | KNO$_3$ 0.01 M<br>pH 7 | MGL<br>pH 7.2 | LD<br>pH 6.8 |
|---|---|---|---|---|
| A-sample 1 | −5.0 | −4.5 | −5.0 | −3.0 |
| B-sample 1 | −5.0 | −5.0 | −5.4 | — |

*1 Unit = $10^{-8} m^2 V^{-1} sec^{-1}$

For contact angle measurements, small drops (1 microliter) of distilled water were deposited on the flat, horizontal surface of the samples. The height (h) and width (w) of the base of the drop were measured on a magnified picture projected on a screen. The contact angle ($\phi$) between the solid surface and the tangent to the drop at the solid-liquid-9as contact point, is calculated by means of the equation $$\phi = 2 \arctan \frac{2h}{w}$$

The higher the value of $\phi$, the more hydrophobic is the surface. The results were: Latex A, sample 1, 122°±7°; Latex B: sample 1, 119° ±4°.

The invention is illustrated by the following Examples:

EXAMPLE 1

This Example describes the immobilisation of L-methionine gamma lyase on polymer particles and the use of the immobilised enzyme in a biosensor to determine L-methionine.

L-methionine gamma-lyase solution was provided by Dr. K. Soda, Institute for chemical Research, Kyoto University, Uji, Kyoto-Fu 611, Japan. It has a molecular weight of about 172,000 and consists of four subunits with identical molecular weights. It contains 4 mol of pyridoxal 5'-phosphate per mole of enzyme (Soda et al, Anal. BioChem, 1984, 138, 421–4).

The medium of the enzyme solution (Medium M) was 0.1M potassium phosphate buffer at pH 7.2, containing 20 micro-M pyridoxal phosphate, 0.01% 2-mercaptoethanol, lmM EDTA and 2% ethanol.

Enzymatic activity was determined by introducing into a tube 1 ml of a 0.2M potassium phosphate buffer solution, 500 microliters of 0.1 M L-methionine, 100 microliters of 0.1 mM pyridoxal phosphate and 50 microliters of enzyme solution, followed by dilution with water to a total volume of 2 ml.

The tube was incubated at 37° C for 10 minutes and the reaction then terminated by the addition of 0.25 ml of 50% tri-chloroacetic acid. After centrifugation, alpha-ketobutyrate in the supernatant was determined using 3-methyl-2-benzothiazoline hydrazone as described by Soda, Analytical BioChemistry (1968), 25, 228–235. One unit of enzyme activity (U) corresponds to the production of 1 micromole of alpha-ketobutyrate in 1 minute.

Latices were washed three times with Medium M referred to above by centrifuging and resuspension to give finally a latex containing 10 mg polymer/ml.

Adsorption of the enzyme by the latex was measured by mixing 0.1 ml each of the latex and the enzyme solution and making up to a volume of 1 ml by the addition of Medium M in a tube having a volume of 3.5 ml. The mixture was left for 1 hour at ambient temperature and then centrifuged at $10^4$ rpm for 15 minutes to give a compacted pellet of latex particles in the base of the tube and a supernatant solution. The activity of the adsorbed enzyme was measured by washing the pellet once with Medium M, redispersing the pellet in Medium M to a volume of 0.5 ml, and then determining enzyme activity in the suspension by the method described above for the original enzyme solution.

Results obtained are set out in the table below. The first line gives a summary of results with 18 samples of the latex, each of 3.75 mg. The second line is a summary of results with 2 samples each of 1.75 mg. The third, fourth and fifth lines show the results with one sample each of 1.5 m9, 2.5 mg and 3.75 mg respectively.

| Latex | mg. of carrier | Initial Activity in solution | Activity on pellet | Activity per mg. of carrier |
|---|---|---|---|---|
| A | 3.75 | 1.42 ± 0.2 | 1.33 ± 0.3 | 0.36 ± 0.06 |
| Sample 1 | 1.75 | 1.33 ± 0.03 | 0.725 ± 0.07 | 0.48 ± 0.06 |
| B | 1.50 | 1.8 | 0.9 | 0.6 |
| Sample 1 | 2.50 | 1.8 | 0.8 | 0.32 |
|  | 3.75 | 2.1 | 1.9 | 0.50 |

The use of L-methionine gamma lyase immobilised on a latex in accordance with the invention in a biosensor for the determination of L-methionine, was investigated using the apparatus of FIG. 1(a) described above.

To prepare immobilised enzyme for use in the determination of L-methionine, Latex A described above was washed three times with distilled water by centrifugation and redispersion, giving a final dispersion containing 10% by weight of polymer solids. Approximately 0.1 mg of enzyme was added to 700 mg of the final dispersion, and the mixture was allowed to stand at room temperature for 2 hours. It was then centrifuged and the supernatant liquid was decanted from the pellet of sediment.

Figure 3:
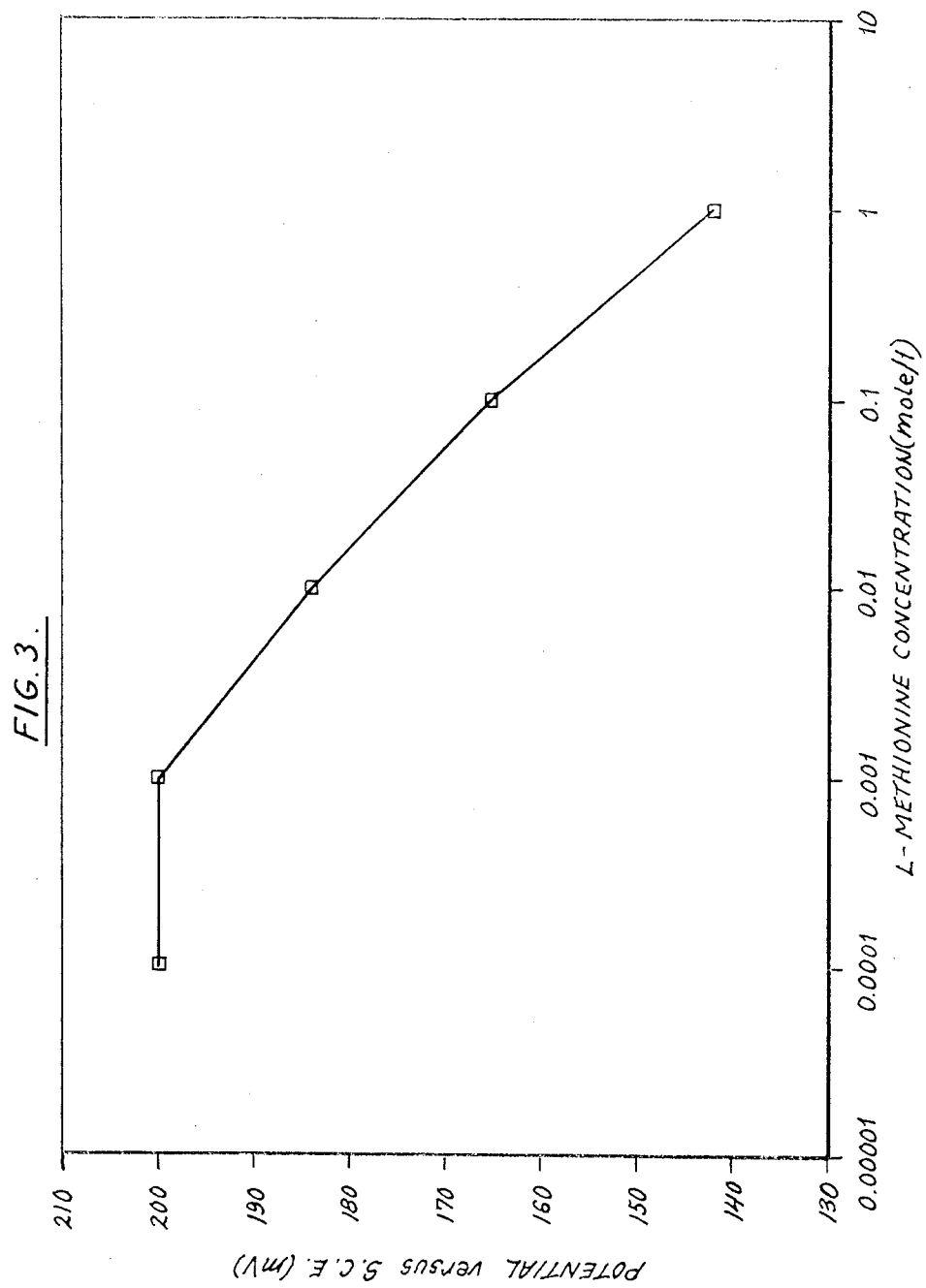
FIG. 3 is a graphic illustration of potential difference 30 minutes after the introduction of an enzyme against the concentration of L-methionine with a buffer pH of 7.
Figure 4:
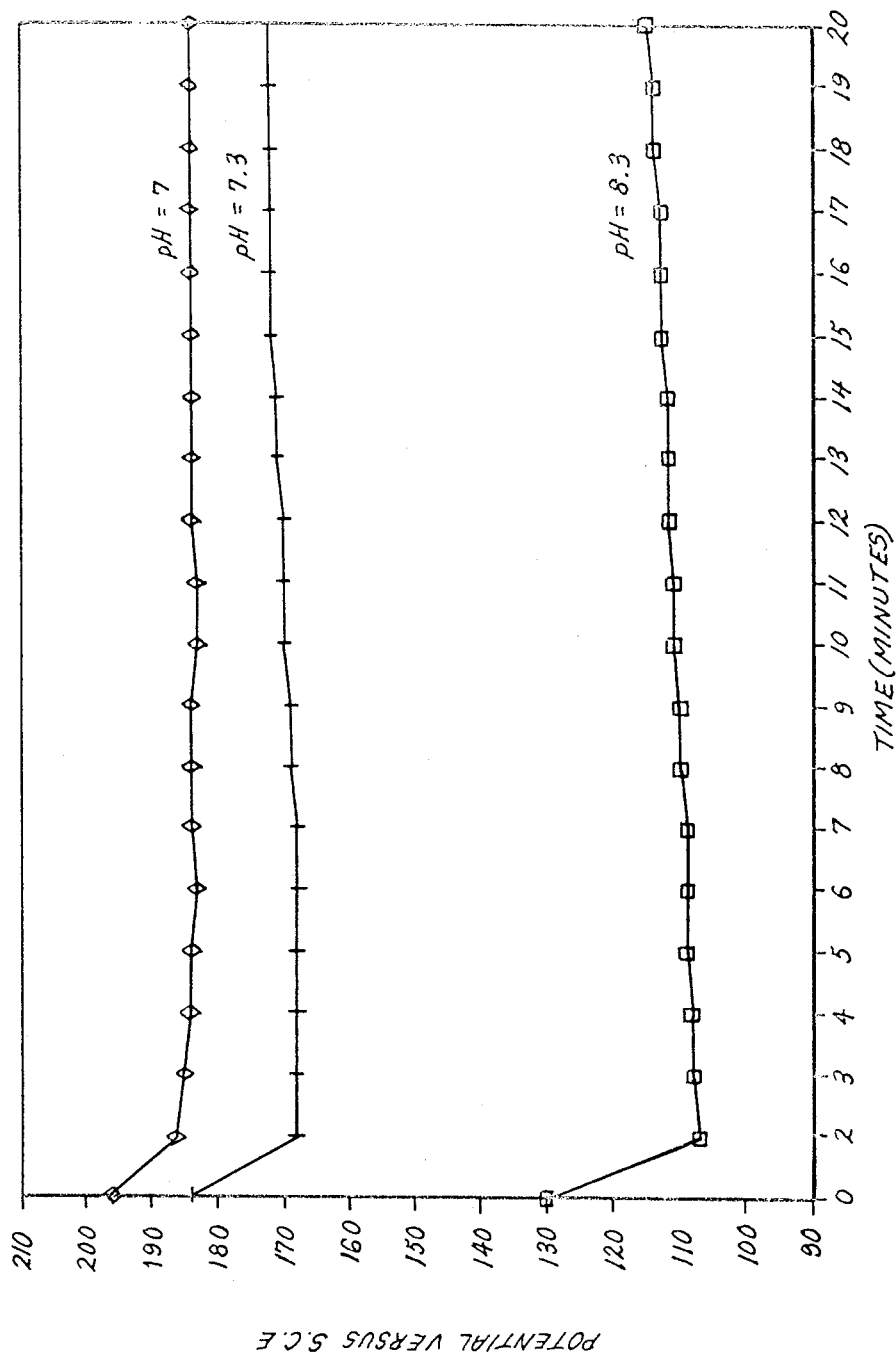
FIG. 4 is a graphic illustration of potential difference against time at a fixed concentration of L-methionine with buffer solutions at various pH values.

The chamber of the half cell of FIG. 1(a) was immersed in a $10^{-3}$ molar solution of phosphate buffer at a temperature of 25° C., together with a standard calomel electrode placed adjacently. The electrodes were connected to a pH meter, and the potential difference between the electrodes was noted. The procedure was repeated with a series of $10^{-3}$ molar phosphate buffer solutions containing $10^{-4}$ molar pyridoxal-5-phosphate and various concentrations of L-methionine. In other experiments, the effect of varying the pH of the buffer at a fixed ($10^{-2}$M) concentration of L-methionine was investigated. In each experiment in the series, a pellet of immobilised enzyme, prepared as described above, was introduced into the chamber of the half cell through the opening ((4) in FIG. 1(a)) after immersion of the half cell in the solution. The potential difference between the electrodes before the introduction of the pellet was noted, and the potential difference was recorded at intervals after its introduction. The results obtained are shown in FIGS. 2, 3 and 4.

Figure 2:
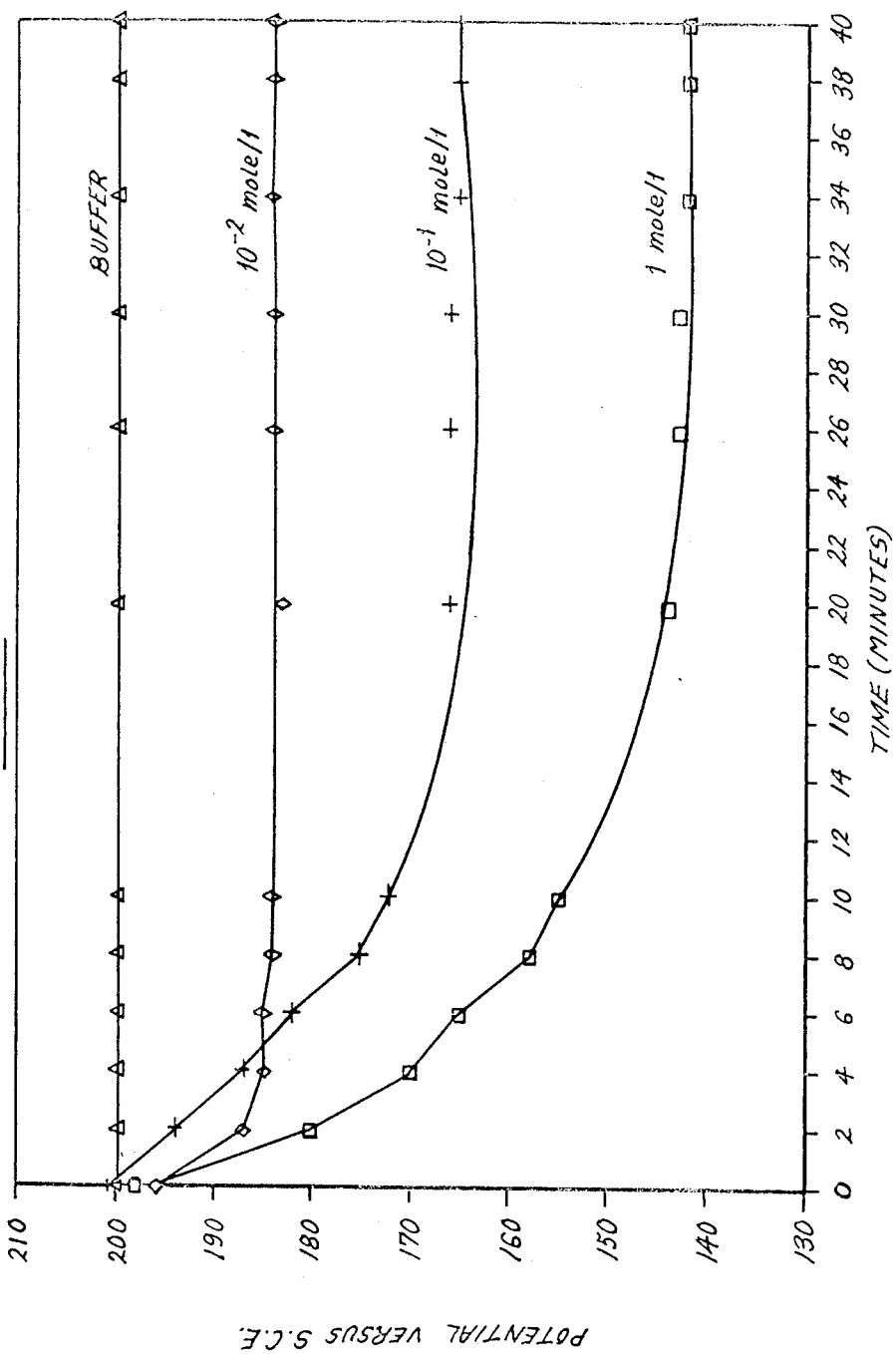
FIG. 2 is a graphic illustration of potential difference against time at a pH of 7 and various concentrations of L-methionine.

FIG. 2 shows the direct plot of potential difference against time at a buffer pH of 7 and various concentrations of L-methionine. Fi9 3 is a plot of the potential difference 30 minutes after the introduction of the enzyme against the concentration of L-methionine with a buffer pH of 7. FIG. 4 is a plot of potential difference against time at the fixed concentration of L-methionine with buffer solutions at various pH values.

EXAMPLE 2

This Example describes the use of L-lysine decarboxylase immobilised on polymer particles in a biosensor to determine L-lysine.

The enzyme used in these experiments was L-lysine decarboxylase Sigma type VIII available from Sigma Corporation, U.S.A.

A sample of latex A above was centrifuged and the sediment was redispersed in a phosphate buffer solution of pH 6. Centrifugation and redispersion were repeated twice.

5 ml of the final dispersion, containing 10% by weight of solids, was mixed with 4.4 mg of L-lysine decarboxylase and the mixture was allowed to stand at room temperature for 1 hour. It was then centrifuged, and the supernatant liquid was decanted from the pellet of sediment.

Figure 5:
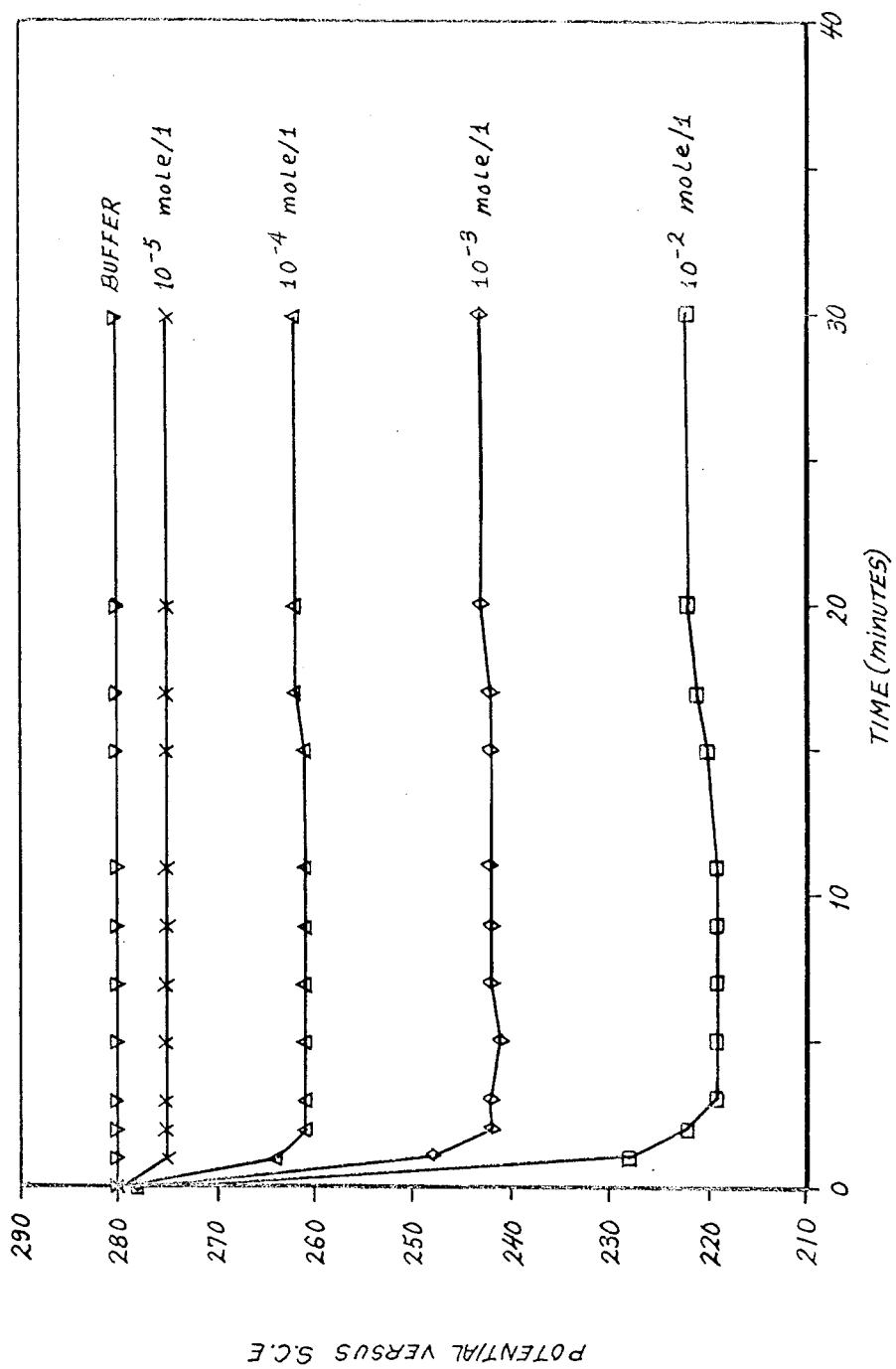
FIG. 5 is a graphic illustration of potential difference against time at different L-lysine concentrations.

The chamber of the half-cell of FIG. 1 (a) was immersed in a $10^{-2}$ molar solution of phosphate buffer at pH 5.92 and a temperature of 37° C, together with a standard calomel electrode placed adjacently. The electrodes were connected to a pH meter, and the potential difference between the electrodes was noted. The procedure was repeated with a series of $10^{-2}$ molar phosphate buffer solutions containing $10^{-4}$ molar pyridoxal-5-phosphate and various concentrations of L-lysine. In each experiment in the series, a pellet of immobilised enzyme, prepared as described above, was introduced into the chamber through the opening (4) in FIG. 1 (a) after immersion of the half cell in the solution. The potential difference between the electrodes before the introduction of the pellet was noted and the potential difference was recorded for up to 20 minutes after its introduction. The results obtained are shown in FIG. 5 and 6. FIG. 5 shows direct plots of potential difference against time at the different L-lysine concentrations. FIG. 6 is a plot of the value of the potential difference 5 minutes after the introduction of the enzyme against the concentration of L-lysine.

EXAMPLE 3

This Example describes the immobilisation of L-aspartase on polymer particles.

L-aspartase extracted from Hafnia alvei (Bacterium cadaveris) was purchased from Sigma. L-aspartase has a molecular weight of 180000, an isoelectric point of 4.8 and optimum pH 7.8. The enzyme was dissolved in a phosphate buffer 0.1M ($KH_2PO_4 + K_2HPO_4$) pH 7.2 and divided into portions which were frozen until required for use.

The enzymatic activity assay is based on the following reaction:

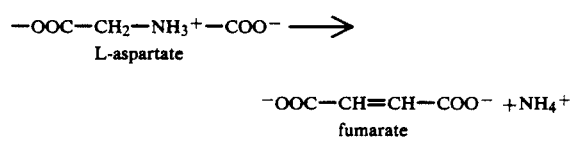

$$-OOC-CH_2-NH_3^+-COO^- \longrightarrow$$
L-aspartate $$-OOC-CH=CH-COO^- + NH_4^+$$
fumarate and is measured by the fumarate production. One activity unit (U) converts 1.0 umole of of L-aspartate to fumarate per minute.

The measurement is carried out by introducing the following reagents into a quartz cell (1 cm light path):
1 ml-0.15 M Tris buffer. pH 8.5
100 ul-0.6 M $MgSO_4.7H_2O$ solution
100 ul-3mM EDTA disodium salt solution
300 ul-0.5 M L-aspartate substrate solution
1.4 ml-$H_2O$,
mixing by inversion, adding 100 ul enzyme solution, and diluting to obtain about 0.2 U or 100 ul of resuspended pellet. The contents of the cell are immediately mixed by inversion and the increase of absorbance (A*) at 240 nm versus time is recorded.

A linear increase in absorbance with time is observed. The units of enzymatic activity in the cell are given by the formula $$\frac{A^* \times 3}{2.53 \times time}$$

where 2.53 is the extinction coefficient of potassium fumarate ($mM^{-1} \cdot cm^{-1}$) and 3 is the final volume of the reaction mixture (ml).

Latex A was washed three times with 0.1 M phosphate buffer (pH 7.2) by centrifuging and resuspension. Adsorption of the enzyme by the latex was measured by adding a portion of enzyme solution having a predetermined activity to 3.75 ml of latex and making up the volume to 1 ml by the addition of buffer solution. The mixture was left for 1 hour at ambient temperature and then centrifuged at $10^4$ rpm for 15 minutes to give a compacted pellet of polymer particles and a supernatant solution. The activity of the adsorbed enzyme was measured by washing the pellet once with the buffer, resuspending in a volume of 250 ul and then applying the method described above. In a second investigation, the above procedure was repeated using a phosphate buffer having a pH of 8.0.

|              | Activity in initial solution (U) | Activity in pellet (U) |
| --- | --- | --- |
| (a) pH = 7.2 | 0.26 | 0.019 |
|              | 0.30 | 0.014 |
|              | 0.30 | 0.015 |
|              | 0.23 | 0.015 |
| (b) pH = 8.0 | 0.30 | 0.015 |

The results indicate that a comparatively small fraction of the enzyme is adsorbed on the latex by this procedure. However, concurrent determinations of the residual enzymatic activity in the supernatant solution and of the total protein adsorbed suggested that proteins that are impurities in the commercial aspartase were adsorbed preferentially. Addition of a second portion of latex to the supernatant liquid would be expected to result in a higher value of the activity per mg carrier for this second portion.

EXAMPLE 4

Experiments on the adsorption of L-trytophanase on latex A indicated that proteins that are impurities in the commercially-purchased enzyme are preferentially adsorbed relative to the enzyme itself when using washed but otherwise untreated latex. Pretreatment of the latex with aluminium nitrate improved the selectivity but without significantly increasing the amount of active enzyme adsorbed per unit of carrier. The treatment with aluminium nitrate had little effect on the electrophoretic mobility of the latex, but increased the hydrophobicity of the particles as shown by an increase in the angle of contact of a water droplet with a surface formed by drying and compacting the latex particles from about 125° to about 163°.

What is claimed is:

1. An electrosensor for use in assaying an amino acid selected from L-methionine, L-lysine, L-aspartic acid and L-tryptophan comprising a pH-sensitive electrode located in a sensing zone containing in aqueous dispersion a latex of polymer particles having an enzyme corresponding to the amino acid being assayed immobilized thereon by having been contacted with latex polymer particles having a surface charge such that electrophoretic mobility of the latex particles has a negative value of $-2.0 \ 10^{-8}m^2V^{-1}sec^{-1}$ or below when measured at pH 7 in 0.01M $KNO_3$ and a polymer solids concentration of 30 mg/l, and having a hydrophobic surface such that the contact angle of a 1 microliter droplet of distilled water with a plane horizontal surface formed by drying and compacting the latex particles is 70° or more.

2. An electrosensor according to claim 1 in which the pH-sensitive electrode is a metal/metal oxide electrode.

3. An electrosensor according to claim 2 in which the pH-sensitive electrode comprises iridium oxide on iridium or titanium, and the iridium oxide has a coating of a perfluoro-sulfonate polymer.

4. A method of assaying an amino acid selected from L-methionine, L-lysine, L-aspartic acid and L-tryptophan which comprise the steps of
    (a) introducing an aqueous solution containing the amino acid into a sensing zone of an electrosensor having a pH-sensitive electrode and a reference electrode and said zone containing in aqueous dispersion a latex of polymer particles having an enzyme corresponding to the amino acid being assayed immobilized thereon by having been contacted with latex polymer particles having a surface charge such that electrophoretic mobility of the latex has a negative value of $-2.0\ 10^{-8} m^2 V^{-1} sec^{-1}$ or below when measured at pH 7 in 0.01M $KNO_3$ and a polymer solids concentration of 30 mg/l, and having a hydrophobic surface such that the contact angle of a 1 microliter droplet of distilled water with a plane horizontal surface formed by drying and compacting the latex particles is 70° or more, (b) measuring the change in the potential difference between the pH-sensitive electrode and the reference electrode over a fixed time interval, and (c) said change with the amount of amino acid in aqueous solution.

5. The method of claim 4 wherein the sensing zone also contains pyridoxal-5-phosphate as a co-enzyme.

* * * * *